United States Patent
Stein et al.

(10) Patent No.: US 6,385,283 B1
(45) Date of Patent: May 7, 2002

(54) DEVICE AND METHOD FOR DETERMINING FUTURE FRACTURE RISK

(75) Inventors: Jay A. Stein, Boston; Eric Von Stetten, Stow; Howard P. Weiss, Newton; John P. Fallon, Andover; Andrew P. Smith, Medford; Kevin E. Wilson, Cambridge, all of MA (US)

(73) Assignee: Hologic, Inc., Bedford, MA (US)

( * ) Notice: Subject to any disclaimer, the term of this patent is extended or adjusted under 35 U.S.C. 154(b) by 0 days.

(21) Appl. No.: 09/448,959

(22) Filed: Nov. 24, 1999

(51) Int. Cl.$^7$ ............................................... G01B 15/02
(52) U.S. Cl. ............................ 378/54; 378/51; 378/56; 378/89; 378/174
(58) Field of Search ............................. 378/51, 54, 56, 378/89, 174, 207

(56) References Cited

U.S. PATENT DOCUMENTS

| | | | | |
|---|---|---|---|---|
| 4,811,373 A | * | 3/1989 | Stein | 378/54 |
| 4,829,549 A | * | 5/1989 | Vogel et al. | 378/55 |
| 5,673,298 A | * | 9/1997 | Mazess | 378/54 |
| 5,771,272 A | | 6/1998 | Berger et al. | |
| 5,778,045 A | | 7/1998 | von Stetten et al. | |
| 5,785,041 A | | 7/1998 | Weinstein et al. | |
| 5,835,555 A | | 11/1998 | Barry et al. | |
| 5,838,765 A | | 11/1998 | Gershman et al. | |
| 5,850,836 A | | 12/1998 | Steiger et al. | |
| 6,029,078 A | * | 2/2000 | Weinstein et al. | 600/407 |
| 6,102,567 A | * | 8/2000 | Cabral et al. | 378/197 |

OTHER PUBLICATIONS

Hologic, S–149 International (Mar. 1999) "QDR 4500 Clinical Bone Densitometer".

S.R. Cummings et al. —The New England Journal of Medicine, Mar. 23, 1995, vol. 332, No. 12, pp. 767–773 "Risk Factors for Hip Fracture in White Women".

C.C. Gluer et al. —Radiology 1996;199:725–732 "Osteoporosis: Association of Recent Fractures with Quantitative US Findings".

D.C. Bauer et al. —Archives of Internal Medicine Mar. 24, 1997, vol. 157, pp. 629–634 "Broadband Ultrasound Attenuation Predicts Fractures Strongly and Independently of Densitometry in Older Women".

J.A. Kanis —Osteoporosis Int. (1997) 7:390–406 Guidelines for Diagnosis and Management Osteoporosis.

J.A. Kanis —Osteoporos Int. (1997) 7 (Suppl. 3):S108–S116 "Diagnosis of Osteoporosis".

National Osteoporosis Foundation Guidelines 1998 —Fig. 4.

Merrill's Atlas of Radiographic Positions and Radiologic Procedures 9th ed. vol. 1, pp. 420–421.

M.C. Nevitt et al. —Bone vol. 25 No. 5, Nov. 1999:613–619 "Association of Prevalent Vertebral Fractures, Bone Density, and Alendronate Treatment with Incident Vertebral Fractures: Effect of Number and Spinal Location of Fractures".

P.D. Ross et al. —Osteoporosis Int. (1993) 3:120–126 "Predicating Vertebral Fracture Incidence from Prevalent Fractures and Bone Density Among Non–Black, Osteoporotic Women".

S.J. Jacoben et al. —Epidemiology 1992 Nov; 3 (6):515–8 "Hospitalization with vertebral fracture among the aged: a national population–based study, 1986–1989".

(List continued on next page.)

Primary Examiner—David V. Bruce
Assistant Examiner—Pamela R. Hobden
(74) Attorney, Agent, or Firm—Cooper & Dunham LLP (57) ABSTRACT

A DEXA bone densitometer produces estimates of future fracture risk from a current fracture data derived from a lateral image of a patient's thoracic and lumbar spine taken in a single scan, typically with the patient on her or his side, and from numerical bone mineral density measurements.

27 Claims, 4 Drawing Sheets

OTHER PUBLICATIONS

M.A. Kotowicz et al. —Journal of Bone and Mineral Research vol. 9, No. 5, 1994 "Risk of Hip Fracture in Women with Vertebral Fracture".

L.J. Melton III, et al. —Osteoporos Int. (1999) 10:214–221 "Vertebral Fractures Predict Subsequent Fractures".

QDR 4500 Image Works —View User's Guide —Hologic Doc. No. 080–0570 Rev. C —Copyright 1996.

* cited by examiner

DEVICE AND METHOD FOR DETERMINING FUTURE FRACTURE RISK

FIELD

This patent specification relates to the general field of osteoporosis diagnosis, bone density, and vertebral imaging, and in particular to using a single device to predict future fracture risk by combining several measurements made on a single device along with biographical and/or other information about a patient to produce an estimate of the patient's future risk of bone fracture.

BACKGROUND

Dual-energy bone densitometers such as the QDR machines manufactured by the assignee hereof, Hologic Corporation of Bedford, MA, and similar devices manufactured by LUNAR Corporation and Norland Corporation are used to measure Bone Mineral Density (BMD) and Bone Mineral Content (BMC) of the spine, hip, and peripheral sites. See, e.g., U.S. Pat. Nos. 5,771,272, 5,778,045, 5,835, 555, and 5,838,765, which are hereby incorporated by reference. These devices use the information from a particular BMD measurement at a particular site to classify patients with respect to their risk for future fractures. Further, some of the bone densitometer machines, namely the QDR4500A by Hologic and the Expert by LUNAR are capable of imaging the spine in the supine lateral position. The image of the spine thus obtained is used for quantitative morphometric analysis by the placing of points on the image and measuring morphometric parameters as discussed, for example, in U.S. Pat. Nos. 5,850,836, 5,673,298, and 5,483, 960, which are hereby incorporated by reference. These quantitative morphometric measurements may be combined with values related to the bone mass to indicate the likelihood of future vertebral fractures in the vertebra. However, in spite of attempts at automating the calculation of morphometric indicia and the placement of points on the digital image provided by the bone densitometers, the procedure of quantitative morphometry to determine vertebral deformity (or fracture) can be labor intensive and tedious. Further, some of the bone densitometry machines use both a single energy and dual energy scan of the lumbar-thoracic spine. The single energy scan is faster and has a lower dose, but in the thoracic part of the spine soft tissue can sometimes obscure the vertebral endplates. The dual-energy scan subtracts out the soft tissue artifacts seen in the thoracic region and displays only the bone image. But dual-energy imaging, because it is effectively a difference of two images, has difficulty obtaining a high enough signal-to-noise ratio in the lumbar region of thicker patients using the low dose x-ray sources typically employed in densitometry. Besides morphometric imaging in the supine lateral position (patient lying on her or his back), some bone densitometers (e.g. QDR4500C by Hologic) have an imaging mode that allows imaging of the vertebral column while the patient is in a decubitus position, lying on her or his side. This positioning of the patient allows the physician to look for fractures in much the same way as when a supine lateral view is taken. There are services available on the Internet or through software licenses that combine information obtained from BMD measurements, information about significant prevalent fractures, ethnicity and age of a patient to calculate Remaining Lifetime Fracture Probability (RLFP). In the service located at www.medsurf.com, the physician types in information about the patient and the software generates a report, which includes an estimate of the likelihood of future fractures. In particular, this software emphasizes the probability that a patient, typically a woman, will have a fracture during her remaining lifetime. Many other methods of reporting fracture have been discussed in the literature and include the probability of a fracture within a specified time frame (e.g., 1 year), the relative risk of fracture compared to other patients of the same sex, ethnicity, and age, or simply qualitative measures such as not increased, increased, and high risk compared to a reference population (which may or may not have the same sex, age, and/or ethnicity). Factual bases for determining a patient's future risk of fracture are discussed in many studies of a relationship between future fracture risk and such factors as age, sex, ethnicity, BMD, prevalent vertebral fracture, maternal history of fracture, corticoid use, etc. Other information can also be used for fracture risk estimates, including information from ultrasound bone units such as the Sahara unit manufactured by Hologic and from biochemical test strips. See, e.g., U.S. Pat. No. 5,785,041, incorporated herein by reference. Fracture risk can also be divided by fracture site, with hip fractures often being a separate category because of the significant cost and morbidity associated with this type of osteoporotic fracture.

The following documents may be of interest to the device and method disclosed herein, and are hereby incorporated by reference: (1) J. A. Rea et. al.—Bone Vol. 23, Number 5, Supplement pg. S160; (2) S. R. Cummings et. al. The New England Journal of Medicine, Mar. 23, 1995 Vol. 332 No. 12 "Risk Factors for Hip Fracture in White Women;" (3) C. C. Gluer et. al.—Radiology 1996; 199:725–732 "Osteoporosis: Association of Recent Fractures with Quantitative US Findings;" (4) D. C. Bauer et. al., Archives of Internal Medicine Mar. 2, 1997, Vol. 157 Pg. 629 "Broadband Ultrasound Attenuation Predicts Fractures Strongly and independently of densitometry in Older Women;" (5) H. Genant et al.—Journal of Bone and Mineral Research Vol. 8, Number 9, 1993, pg. 1137 and J. Bone and Mineral Research Vol. 11 Number 7, 1996; (6) J. A. Kanis—Osteoporsis Int. (1997) 7:390–406 "Guidelines for diagnosis and management of Osteoporosis;" (7) J. A. Kanis Osteoporosis International (1997) 7 (Suppl. 3):S108–S116 "Diagnosis of Osteoporosis;" (8) National Osteoporosis Foundation Guidelines 1998 (see, e.g., FIG. 4); (9) Merrill's Atlas of Radiographic Positions and Radiologic Procedures 9th ed. Vol.1 pg. 420–421; (10) M. C. Nevitt et. al. Bone Vol. 25 No. 5, November 1999:613–619; (11) P. D. Ross et. al. Osteoporosis Int. (1993) 3:120–126 "Predicting Vertebral Fracture Incidence from Prevalent Fractures and Bone Density among Non-Black, Osteoporotic Women;" (12) S. J. Jacobsen et. al. Epidemiology 1992 3(6):515-8 "Hospitalization with vertebral fracture among the aged: a national population-based study;" (13) M. A. Kotowicz et. al., Journal of Bone Mineral Research "Risk of hip fracture in women with vertebral fracture;" (14) P. D. Ross et. al. Osteoporosis International 1993; 3(3): 120–126 "Predicting vertebral fracture incidence from prevalent fractures and bone density among non-black, osteoporotic women;" (15) L. J. Melton 3rd, et. al. Osteoporosis International 1999 10(3):214–221 "Vertebral Fractures Predict Subsequent Fractures;" (16) The Merck Manual of Geriatrics—Section 82 "Disorders of Mineral Metabolism" www.merck.com/pubs/mm_geriatrics/toc.htm; (17) FDA 510k—FDA premarket notification k9972775 clearance date Oct. 1, 1999. MXA-II software option; (18) QDR 4500 Image Works—View User Guide Hologic Doc. No. 080-0570 Rev. C Copyright 1996.

SUMMARY

This patent specification discloses a device and a method in which an integrated device that not only measures bone mineral density (BMD) and provides an image that is useful for determining prevalent vertebral fractures, but also combines the BMD and the prevalent vertebral fracture information with biographical information and/or other risk factors to provide an indicator of a patient's future fracture risk to the physician (or other health services provider). This saves the physician time, prevents transcription errors, and provides a single report that the physician can provide to and discuss with the patient or the patient's referring physician. It also can help increase the accuracy of the diagnosis, since usually risk factors are not completely independent of each other, and could be combined based on relationships found in clinical studies. To combine such risk factors otherwise can be tedious and time consuming, and can require an extensive literature search. Moreover, by summarizing this information along with the scan reports and making this quickly available, the device and method disclosed herein can allow the physician to immediately discuss these results with the patient and can eliminate the need for the patient to have a return visit. Further, this arrangement can provide a single-energy X-ray scan of the entire lumbar-thoracic region, with the operator selecting a part of this region for repeat scanning using a dual-energy X-ray scan mode. This is useful because the single-energy scan is of a much lower dose and is much quicker, and only sometimes will it be necessary to repeat a certain part of the scan with a dual-energy scan. Thus, dose to the patient and time are conserved, especially since scan time for the dual-energy scan is approximately linearly proportional to the length of spine under examination. A typical single-energy high resolution scan requires 12 seconds for 18 inches, compared with 6 minutes for 18 inches for dual-energy on a QDR4500A. Also allowed, is for a scan window to be set on a dual-energy image, and another scan with different technique factors (collimators, dose, dual- or single-energy) performed based on the window set. The arrangement disclosed herein also allows different images to be displayed side by side and compared, for example, a single and dual energy lateral image, or two images taken on different dates.

DESCRIPTION OF PREFERRED EMBODIMENTS

A preferred embodiment uses an x-ray bone densitometer to be offered under the name Delphi by Hologic, which can determine the bone density of a patient and produce a lateral image of a patient's spine with the patient in a decubitus position, lying on her or his side, and the X-rays in a vertically oriented fan-shaped beam using both a single-energy and/or dual-energy X-ray mode. The lateral image can be viewed by the physician to determine prevalent vertebral fractures and thus current fracture data. The study typically consists of, at least, a BMD measurement and a lateral image of the spine. The BMD measurement can be done following the user guide for the QDR 4500 bone densitometer manufactured by Hologic, as described in Hologic Document No. 080-0451 Rev. G and incorporated by reference herein. The lateral image can be obtained by following the QDR 4500 Image Works—View User's Guide Document No. 080-0570 Rev. C and incorporated by reference herein. In performing the scan, the operator can fill in the patient's name, sex, age, ethnicity, height, weight, and other biographical or other data that may be relevant to the physician and this information is displayed on the report and stored with the measurement results in a database. The report can be displayed on a computer monitor and/or printed with a suitable printer or other output device, and can be archived in digital form, such as DICOM format.

The lateral image can be viewed by the physician, either on the computer monitor, or by other high-quality output devices for the presence of vertebral fractures. This can be preferable to the placement of points and quantitative analysis of the morphometry of the image because it is more convenient, expeditious and intuitive. Further, the combination of age, sex, BMD and prevalent vertebral fracture are strong predictors of future fracture risk.

In one embodiment, the device gives the physician the opportunity to input into the database the number of prevalent vertebral fractures seen by the physician in the single or dual-energy image(s). The software combines this information with other information in the database, such as age, sex, ethnicity, BMD of the spine and/or BMD of the hip to produce a report with prediction of future bone fracture risk. The prediction of fracture risk may be relative fracture risk compared to an age, sex and ethnicity matched population, or an absolute fracture risk based on a specific time frame, such as one year or projected remaining lifetime. Alternatively, along with the lateral image of the spine, the device includes in the displayed report fracture risk data such as an indication based on no vertebral fractures, one vertebral fracture, or two or more vertebral fractures. The physician can then view the image for fractures, and determine which future fracture risk applies to this patient. The physician can then write his report based on his findings, incorporating the appropriate future fracture risk.

In another embodiment, the risk of future fractures is expressed as the risk of future hip fractures and the risk of other fractures.

In a further embodiment, other clinical risk factors are input into the database, such as corticoid use, maternal history of osteoporotic fracture, ultrasound measurements of bone quality such as made by the Sahara bone sonometer manufactured by Hologic, results of biochemical markers, serum calcium and albumin levels, estrogen use, alendonate use, lifestyle factors, family history, etc. These additional risk factors are incorporated into the future fracture risk prediction, thus integrating all of the clinical risk factors into a single number (or two if the risk of hip fractures is reported separately). Usually, risk factors are not completely independent of each other, so it is may not be easily apparent to the physician, without a tedious literature search, how each additional risk factor increases or decreases a patient's future fracture risk. For example, the additional relative risk factor of a low ultrasound bone measurement when a patient has a BMD measurement is only about 1.5, while if nothing is known about the patients BMD, the relative risk of a low ultrasound bone measurement is about 2.0 (Bauer 1997 reference). In another embodiment, the value of treatment is incorporated into the risk model. In this embodiment, the doctor is given the patient's future risk of fracture under the assumption of no treatment, or various treatment options which could include life-style modifications, estrogen replacement therapy, or BMD-increasing medications. How much a given treatment option decreases a patient's future fracture risk may be dependent on that patient's specific risk factors. For example, calcium supplementation may significantly reduce the risk factor of a patient who is calcium deficient as evidenced by serum calcium and albumin levels, but have very little effect on a patient who is not calcium deficient.

Another embodiment allows the operator, after finishing the single-energy X-ray scan, to select a part of the spine to scan with a user selected technique factor, for example, in dual-energy mode or in a higher resolution single energy mode. While it may not always be necessary, a different technique scan can be useful in cases of soft tissue artifacts or where there is a motion artifact. By limiting the portion of the spine over which the additional scan is acquired, the dose to the patient and the time of examination can be kept low. This additional scan can be part of the same study as the single-energy scan, and the physician can refer to either image to determine vertebral fractures. In the preferred embodiment, there are two indicators or lines that can be moved on the single energy image with a mouse or other pointing device. These two lines delimit the area of the scan that will be done with a different scan mode. QDR 4500 devices manufactured by Hologic have the ability to use the information, along with the encoders of the instrument, to accurately reposition over the area to be rescanned. After the second image is acquired, the software allows both images to be viewed simultaneously, or for several images to be viewed, even images which were obtained at an earlier date. By comparing images, the physician can diagnose incident fractures on repeated visits, and this can be a method of monitoring treatment efficacy.

Figure 1:
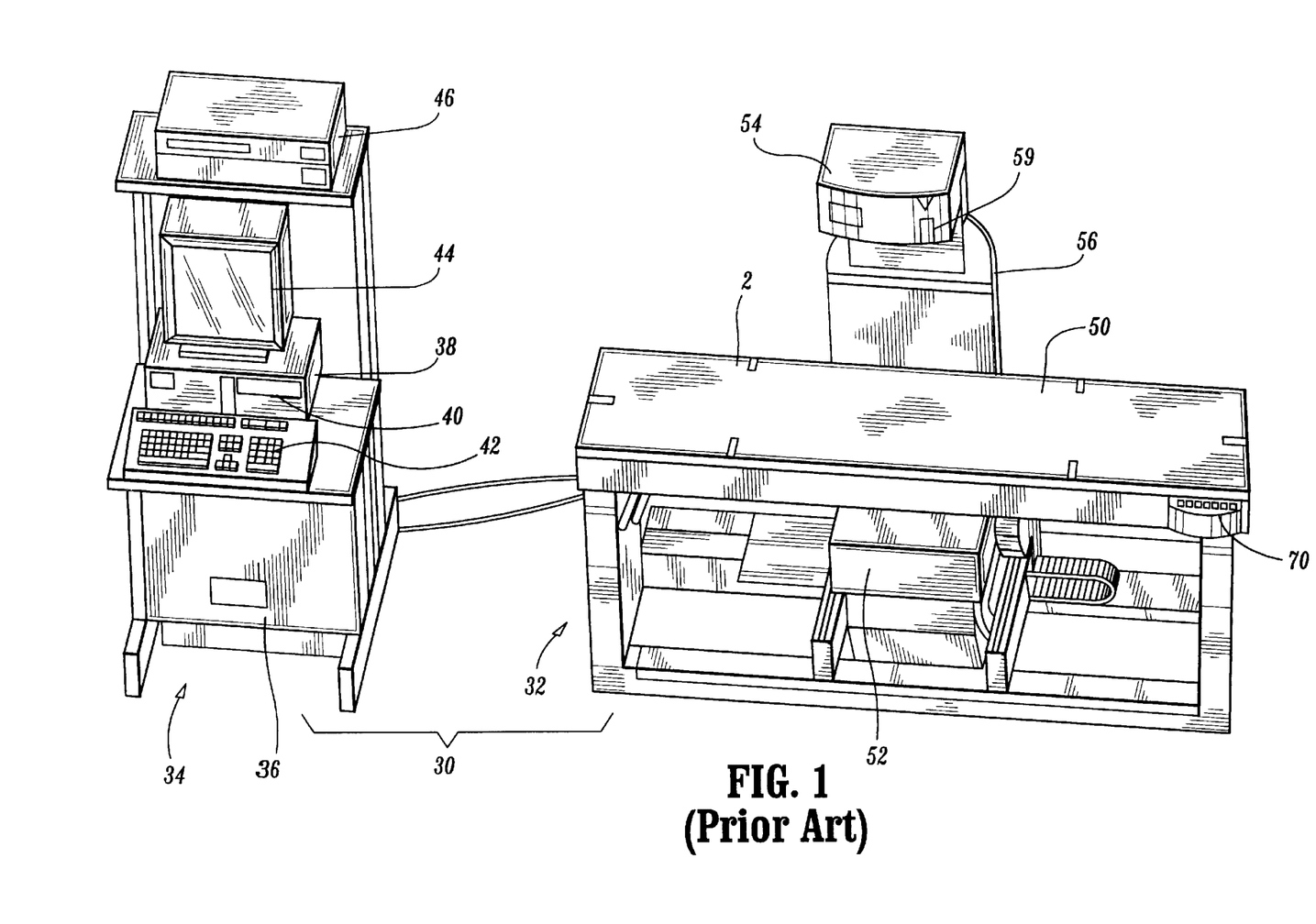
FIG. 1 illustrates a prior art DEXA (dual energy x-ray absorptiometry) system.

Referring to FIG. 1, which illustrates a prior art QDR 4500 x-ray bone densitometer, a scanning system 30 includes a patient table unit 32 comprising a patient table 50 and a C-arm 56 serving as a source-detector support. A workstation 34 controls patient table unit 32 and C-arm 56 and processes scan data into numerical bone density data such as BMD and images. Workstation 34 includes a power supply module 36, a host computer 38 with a mass data storage device 40, an operator console keyboard 42, a display monitor 44 and a printer 46. Table 50 can move up and down and along its long dimension. C-arm 56 also moves along the length of table 50 to scan a patient thereon with a fan beam of x-rays from source 52 so that a detector array 54 and associated electronics can produce dual energy or single energy scan data. The C-arm can also move across the table to correctly position the source and detector over the desired body part.

The Delphi bone densitometer to be offered by Hologic and incorporating an embodiment described in this patent specification is generally similar to the QDR 4500 illustrated in FIG. 1 and described in the patents incorporated by reference, and has two models, one with whole body (Delphi-W) and one without whole body (Delphi-C). The designation Delphi refers to both models. The Delphi C and W correspond approximately to the existing QDR4500 C and QDR4500W, with certain enhancements, some similar to features of QDR4500 SL. For example, the detectors in the Delphi models are approximately half the size as the detectors in the 4500 C and W, providing 2x better image resolution perpendicular to the scan direction, as is the case with the existing 4500 SL model. The Delphi has two collimators (slits), a 1 mm and a 0.5 mm collimator, while the QDR4500C/W have only the 1 mm collimator. The additional 0.5 mm collimator is used to provide better resolution in the direction of scanning., as in the QDR4500 SL model.

The Delphi models provide an Instant Vertebral Assessment feature of the Delphi using the process of future risk estimation discussed above. The Delphi models need not have a rotating C-arm, in which case a lateral view image can be obtained with the patient in the decubitus position, lying on her side instead of her back, which is a well know X-ray technique that can be done well with proper training. An advantage of this position is that certain patients tend to be thinner in the direction of the x-rays than if supine (body mass can hang forward instead of around the sides), and this can reduce image noise and enhance contrast between bone and soft tissue. Another advantage is that the source can be closer to the patient, increasing the magnification and improving the effective image resolution. Another improvement in the Delphi system is an Auto Analysis feature, that can use a region of interest locator of the type described in U.S. Provisional Patent Application Ser. No. 60/148,027, hereby incorporated by reference. This includes improved placement of the femoral neck box. Another improvement is a Dual Hip feature.

Figure 2:
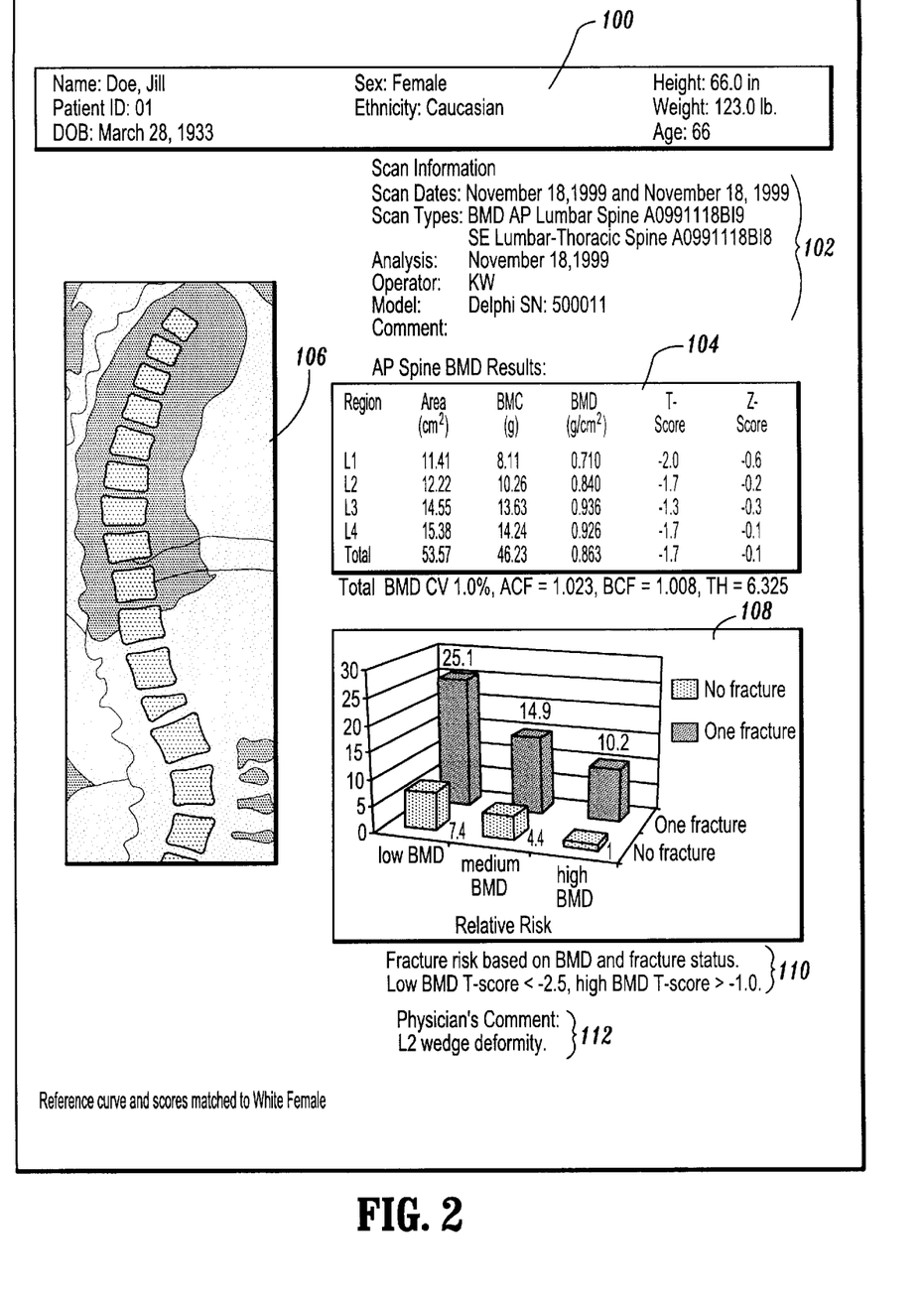
FIG. 2 illustrates a report in accordance with one embodiment of the disclosed device and method.

FIG. 2 illustrates an example of a patient report produced in accordance with an embodiment described in this patent specification. Box 100 contains patient-specific information that can be entered by the operator or can come from a database. At 102, the report shows scan information (which in this illustration is representative rather than specific to a patient or to a scan). Box 104 shows representative numeric bone characteristics data such as BMD estimates for the lumbar vertebrae. A lateral image of the patient's thoracic and lumbar spine is shown at 106, obtained in a single and unidirectional scan at single energy. This image demonstrates a vertebral fracture or deformation, i.e., current fracture data to the effect that this patient has a vertebral fracture or deformation. Box 108 illustrates future bone fracture risk estimates that take into account both numerical bone characteristics data (BMD) and current fracture data. A 3D graph at 108 shows relative future fracture risk (relative to risk of unity for a patient with no current fracture of deformation and high BMD). For this patient, with one fracture, the three columns in the back of the graph are pertinent (relative risk of 10.2, 14.9 and 25.1), and the particular column pertinent to this patient is determined by the patient's numerical BMD data, classified as illustrated at 110, for example. This patient has a medium BMD T-score, so a relative future bone fracture risk of 14.9. The physician can enter comments at 112, for example through keyboard 42, identifying the current fracture or deformity data observed in the image at 106—in this case a wedge deformity at lumbar vertebral body L2.

Figure 3:
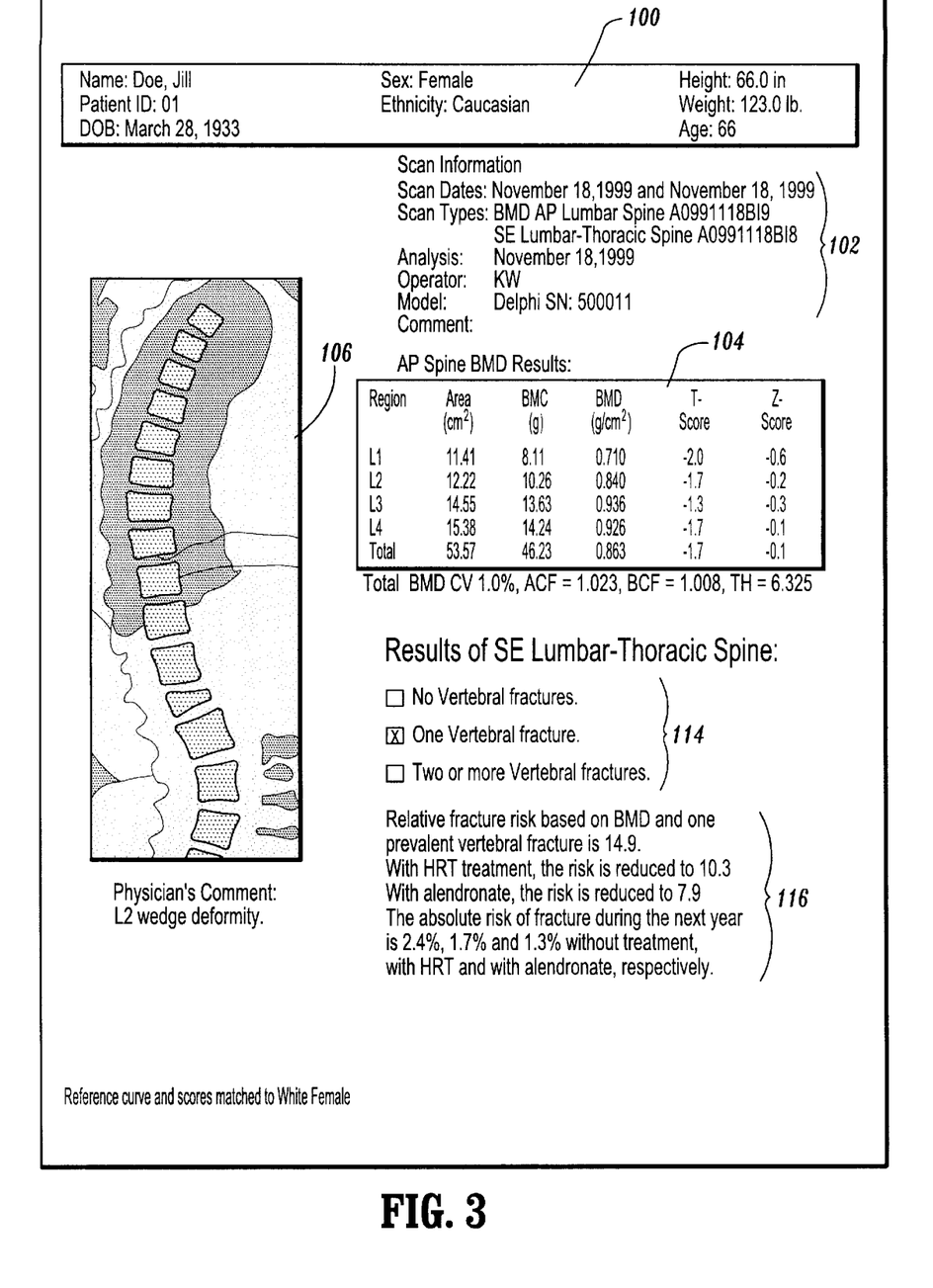
FIG. 3 illustrates another example of a report.

FIG. 3 illustrates another report format that is otherwise similar to FIG. 2 but contains comments that can be automatically generated as a result of the scan data analysis by the densitometer and the entry by the physician of current fracture or deformity data observed in image 106. The densitometer in this case reports the physician's entry of "one vertebral fracture" and automatically generates a report based in that entry and on the BMD estimates, stating in narrative form that the patient's relative risk of future fracture is 14.9 (without treatment). Moreover, the densitometer includes in the report estimates of future fracture risk with different treatment scenarios—with hormone replacement therapy, the relative risk is 10.3 and with alendronate, the relative risk is reduced to 7.9. Still further, the densitometer calculates and prints out in the report at 116, estimates of absolute risk of fracture during the year after the scan in three different scenarios—2.4% without treatment, 1.7% with hormone replacement therapy, and 1.3% with alendronate.

Figure 4:
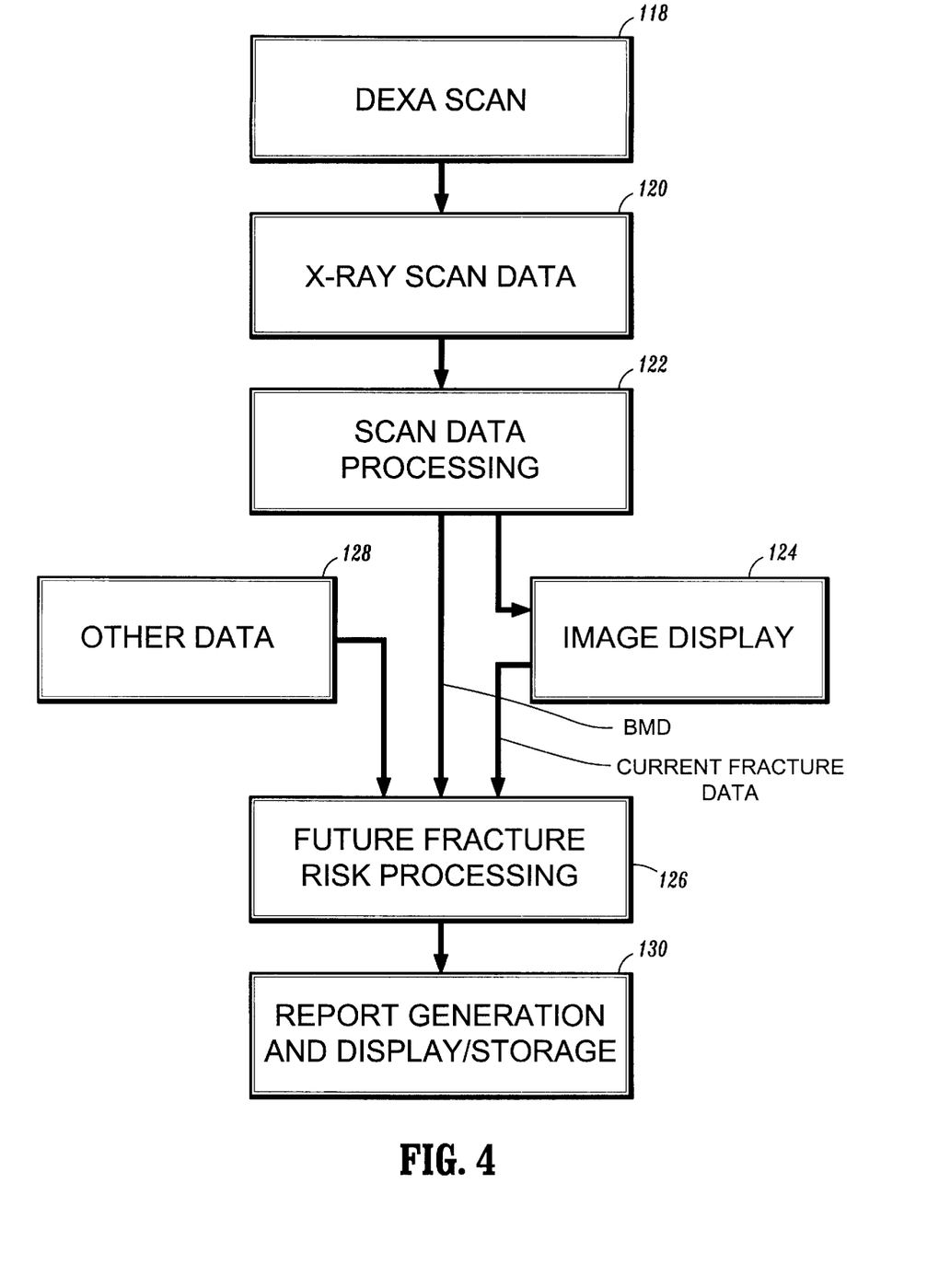
FIG. 4 illustrates main steps in practicing an embodiment of a disclosed method.

FIG. 4 illustrates main steps in a process carried out in a suitably programmed computer, such as computer 36 in FIG.

1, to generate reports such as those illustrated in FIGS. 2 and 3. A patient is scanned with a densitometer such as the Delphi from Hologic at 118, and produces x-ray scan data at 120 that can be dual energy and/or single energy. The scan data includes dual energy data for numerical estimates of bone characteristics as well as single and/or dual energy data for a lateral image of at least a majority of the patient's thoracic and lumbar vertebrae. At 122 the scan data is processed as in known in the art to produce an image displayed at 124 as well as numerical estimates of bone characteristics data such as BMD. Processing step 126 receives such numeric bone characteristics data, as well as current fracture or deformation data provided on the basis of observing the image displayed at 124, or otherwise, and also can receive other data from 128 that can be used in estimating future fracture risk, such as data from biochemical analysis of bone resorption, data from previous patient examinations, etc. Processing step 126 then produces estimates of future bone fracture risk, such as those illustrated in FIGS. 2 and 3, for example by accessing a database relating combinations of inputs to estimates of future fracture risk. At 130, reports such as those illustrated in FIGS. 2 and 3 are displayed and/or printed.

The scan data produced at 120 for the lateral view can be for a single energy image of some or all of the patient's spine, or can include a dual energy image for a part of the spine, for example some or all of the thoracic vertebrae. The dual energy image can be produced by rescanning a part of the spine designated by the operator by markers placed on the single energy image. Alternatively, a part of the spine can be scanned for a single energy image and the remainder scanned for a dual energy image, with the change taking place during the scan, at a point indicated by the operator or detected by the densitometer, for example on the basis of the exposure received at the detector.

While in the preferred embodiments described above the current fracture data is derived from a visual observation of the lateral image, an alternative is to use a known automated or partly automated processes to computer-analyze the scan data for the purpose of detecting vertebral fractures or deformities. Each approach can provide the requisite current fracture data. The reports can be displayed in a number of ways, for example on a monitor or by printing them or by storing them for later viewing or printing or otherwise displaying them, and can be a single page or screen or multi-page reports. While in preferred embodiments the lateral image is taken with the patient recumbent on her or his side on the patient table and the central ray of the x-ray beam generally vertical, it is possible to derive a useful lateral image in other patient positions and x-ray beam orientations, such as with the patient supine and the central x-ray beam generally horizontal.

While various embodiments have been described above, it should be clear that they are merely illustrative of the inventions set forth in the following claims that encompass other variations that are not specifically described above.

What is claimed is:

1. A method of using an x-ray bone densitometer to derive and display each of numerical bone mineral density (BMD) data for the patient, a lateral image of at least a majority of both the lumbar and thoracic vertebrae of the patient, and future bone fracture risk data for the patient, comprising:

using the same x-ray densitometer to scan a patient with x-rays and generate both numerical bone mineral density (BMD) data for the patient and a lateral image of at least a majority of both the lumbar and thoracic vertebrae of the patient;

providing current fracture data relating to the presence or absence of vertebral fractures or deformities in the image;

computer-processing the BMD data and the current fracture data to produce future bone fracture data taking into account both the BMD data and the current fracture data; and displaying a report showing the numeric BMD data, the image, and the future bone fracture risk data.

2. A method as in claim 1 in which the lateral image is taken with the patient recumbent on her or his side.

3. A method as in claim 2 in which the image is a single energy image.

4. A method as in claim 2 in which a selected portion of the image is a single energy image while another portion is a dual energy image.

5. A method as in claim 1 in which the step of scanning the patient to derive said image comprises scanning the patient in a single, unidirectional scan and changing technique factors during the scan.

6. A method as in claim 5 in which the change of technique factors during the scan includes changing from single energy scanning to dual energy scanning during the scan.

7. A method as in claim 5 in which the change of technique factors during the scan includes changing the scanning speed during the scan.

8. A method as in claim 5 in which the change of technique factors during the scan includes changing relative contributions to the image of x-ray measurements in different x-ray energy ranges.

9. A method as in claim 1 in which the report comprises a lateral image of the patient's spine, numerical BMD data of the patients lumbar vertebrae, and a graphical display of the future bone fracture risk data.

10. A method as in claim 1 in which the report comprises a lateral image of the patient's spine, numerical BMD data of the patients lumbar vertebrae, and a narrative display of the future bone fracture risk data.

11. A method as in claim 1 further comprising producing future bone fracture risk data based on selected treatments and displaying in said report the future bone fracture risk in the absence of treatment and in the presence of the respective treatments.

12. A method as in claim 1 in which the lateral image is taken with the patient in a supine position.

13. A method as in claim 1 in which the lateral image is taken with a central ray of the x-rays in a generally vertical orientation.

14. A method as in claim 1 in which the lateral image is taken with a central ray of the x-rays in a generally horizontal orientation.

15. A method as in claim 1 in which the step of using the densitometer to scan comprises using a dual energy densitometer.

16. A method as in claim 1 in which the step of providing current fracture data comprises providing data based on a visual assessment of the lateral image.

17. A method comprising:

scanning a patient with an x-ray bone densitometer to produce x-ray scan data;

using the x-ray scan data to produce both numerical bone characteristic data and a lateral image of both lumbar and thoracic spine of the patient;

using the image to produce current fracture data regarding the presence or absence of vertebral fractures or deformations;

using both the numerical bone characteristic data and the current bone fracture data to produce and display a report indicative both of numeric data regarding current bone characteristics and regarding future bone fracture risk for the patient.

18. A method as in claim 17 in which said scanning comprises scanning both with single energy x-rays and with dual energy x-rays.

19. A method as in claim 18 in which said scanning includes scanning the patient in a recumbent position on the patient's side.

20. A method as in claim 19 in which the scanning comprises scanning a part of the patient's spine with single energy x-rays and a part with dual energy x-rays.

21. A method as in claim 17 in which the scanning comprises changing x-ray technique factors during a single, unidirectional scan of the patient with x-rays.

22. A method as in claim 21 in which the changing of x-ray technique factors during a scan comprises changing from one to the other of single to dual energy scanning.

23. A method as in claim 17 in which the step of using the scan data to produce a lateral image comprises using dual energy x-ray data and different proportions of two x-ray energy ranges for different parts of the image.

24. A system comprising:

a bone densitometer scanner selectively producing x-ray scan data for a lateral image of at least a major portion of the thoracic and lumbar spine of a patient in a single scan and scan data for numerical bone characteristics estimates;

a processor receiving x-ray scan data from the scanner and processing the received data to produce numerical estimates of bone characteristics and a lateral image of at least a major portion of the patient's thoracic and lumbar spine, and responsive both to data regarding said numerical estimates and to data regarding current fractures or deformities in the patient's spine derived from said lateral image to produce estimates of future fracture risk; and a display showing the lateral image as well as said numerical data and said estimates of future fracture.

25. A system as in claim 24 in which the x-ray scan data comprises dual energy data.

26. A system as in claim 24 in which the numerical estimates comprise BMD data.

27. A system as in claim 24 in which the bone densitometer comprises an x-ray source scanning the patient with a generally vertically oriented beam of x-rays to produce the scan data for said lateral image.

* * * * *